(12) United States Patent
Eberlein

(10) Patent No.: US 6,529,195 B1
(45) Date of Patent: Mar. 4, 2003

(54) PAIN MIGRATION TRACKING AND DISPLAY METHOD

(76) Inventor: James B. Eberlein, Zsolna u 26/a, 1125 Budapest (HU)

( * ) Notice: Subject to any disclaimer, the term of this patent is extended or adjusted under 35 U.S.C. 154(b) by 5 days.

(21) Appl. No.: 09/658,466

(22) Filed: Sep. 8, 2000

(51) Int. Cl.⁷ ............................................. G06T 11/40
(52) U.S. Cl. ..................................... 345/441; 600/557
(58) Field of Search ............................. 345/440, 440.1, 345/440.2, 441, 442, 443, 473, 474; 600/407, 410, 425, 501, 607, 557, 587; 283/70, 115, 900, 441; 514/557, 568, 570

(56) References Cited

U.S. PATENT DOCUMENTS

| | | | |
|---|---|---|---|
| 5,339,095 A | * 8/1994 | Redford | 345/158 |
| 5,598,187 A | * 1/1997 | Ide et al. | 345/158 |
| 5,692,500 A | 12/1997 | Gaston-Johansson | |
| 5,829,984 A | 11/1998 | Kawai | |
| 5,873,900 A | 2/1999 | Maurer et al. | |
| 5,894,276 A | * 4/1999 | Altidor et al. | 340/825.22 |
| 5,908,383 A | 6/1999 | Brynjestad | |
| 5,938,690 A | 8/1999 | Law et al. | |
| 5,969,698 A | * 10/1999 | Richard et al. | 345/7 |
| 5,973,676 A | * 10/1999 | Kawakura | 345/173 |
| 5,977,950 A | * 11/1999 | Rhyne | 345/856 |
| 5,984,368 A | 11/1999 | Cain | |
| 6,018,675 A | 1/2000 | Apkarian et al. | |
| 6,031,519 A | * 2/2000 | O'Brien | 345/156 |
| 6,044,303 A | 3/2000 | Agarwala et al. | |
| 6,061,064 A | * 5/2000 | Reichlen | 345/418 |
| 6,072,474 A | * 6/2000 | Morimura et al. | 345/173 |
| 6,094,190 A | * 7/2000 | Kodim | 345/167 |
| 6,107,997 A | * 8/2000 | Ure | 345/173 |
| 6,112,127 A | * 8/2000 | Bennett | 700/86 |
| 6,307,537 B1 | * 10/2001 | Oowada | 345/160 |
| 6,313,864 B1 | * 11/2001 | Tabata et al. | 348/14.02 |

OTHER PUBLICATIONS

Pain Mapping: Details; website, Sep. 1, 2000.
www.pain.com
www.phtcorp. com
www.docucare.net

* cited by examiner

*Primary Examiner*—Jeffery Brier
*Assistant Examiner*—Thu-Thao Havan
(74) *Attorney, Agent, or Firm*—Banner & Witcoff, Ltd.

(57) ABSTRACT

A method of obtaining information from a user connected to a pain-tracking computer through a computer network is provided. A user graphically indicates pain intensity, the location of the pain, and provides input on selected information and/or questions and transmits it to the pain-tracking computer. The pain intensity and location information correspond to pain experienced by the user during different time periods. The pain-tracking computer then creates a color-coded video displaying the pain information.

15 Claims, 5 Drawing Sheets

FIG. 3

Registration

Please enter your name
[ 302 ]

Please enter a password
[ 304 ]

List the names of doctors who may review your data
1. [ 306a ]   3. ☐ more doctors (306c)
2. [ 306b ]   4. ☒ no doctors (306d)

Please enter medical history information by selecting the following link

[ Medical History ] — 308

Please setup your account by selecting the following link

[ Account Setup ] — 310

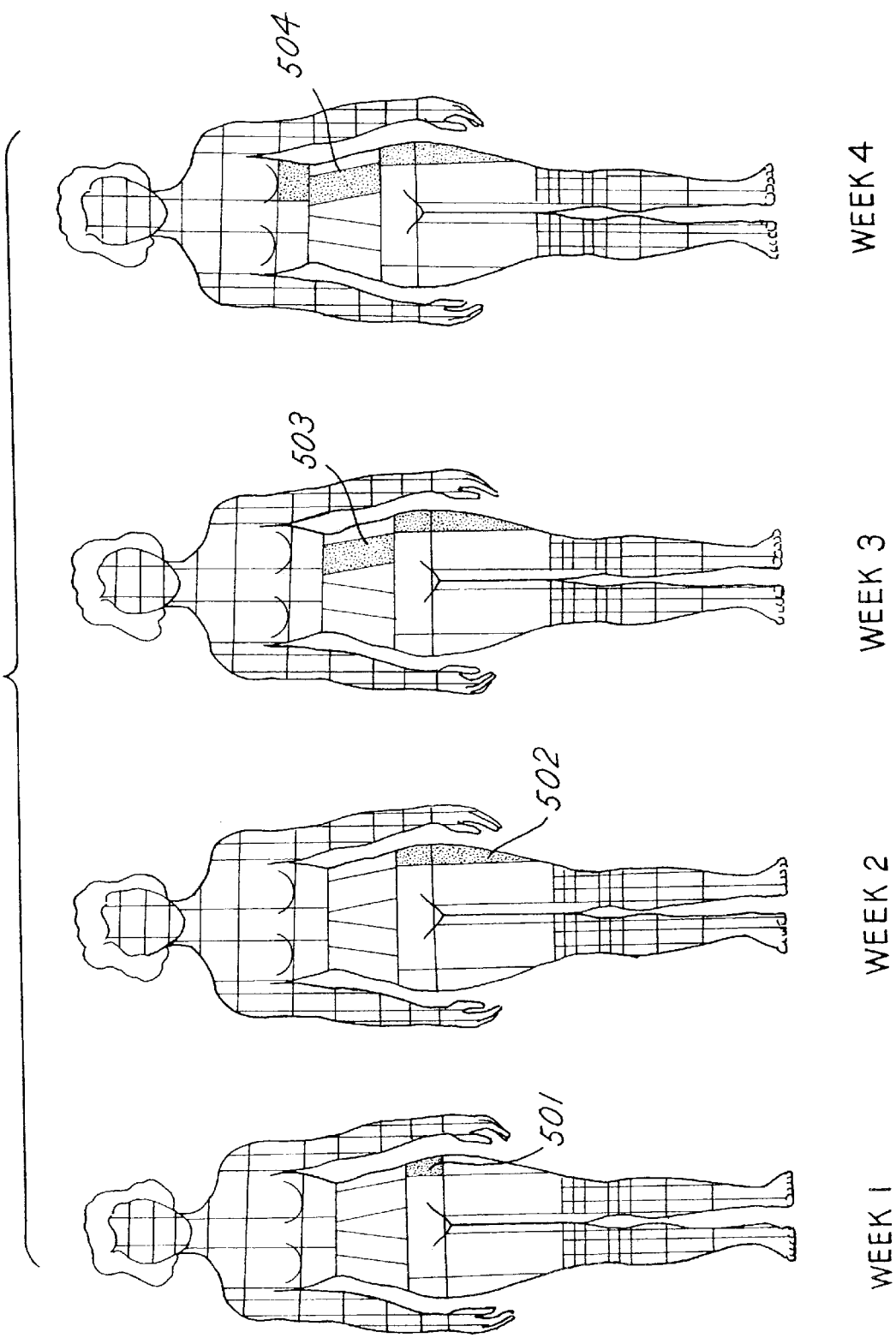

PAIN MIGRATION TRACKING AND DISPLAY METHOD

FIELD OF THE INVENTION

The present invention relates to the field of pain tracking. More specifically, the present invention provides a system that allows users, physicians and healthcare providers to track the location and intensity of pain over a period of time and then play back a historical representation of the user's pain.

BACKGROUND OF THE INVENTION

Physicians and healthcare providers must sort through and evaluate large amounts of information when diagnosing and treating patients with pain disorders. Typically a physician or healthcare provider asks a patient a series of questions to help diagnose the problem and may record certain information on a diagram of the human body. When a patient experiences different degrees of pain over a given period of time, it can be time consuming for the physician or healthcare provider to record all of the information. In addition to consuming a large amount of time, it can be difficult for the physician or healthcare provider to effectively analyze all of the information.

As the amount of information provided to a physician or healthcare provider increases, so does the probability that the physician or healthcare provider will overlook relevant symptoms or fail to recognize a correlation between a symptom and other information provided to the physician or healthcare provider. For example, if a physician or healthcare provider is diagnosing a patient who experiences stomach pain, it may be difficult for the physician or healthcare provider to notice that the patient usually experiences the stomach pain 18 hours after consuming a certain food additive. As a result, the physician or healthcare provider may order the patient to undergo tests that would not otherwise be necessary. Unnecessary tests can be expensive and prolong the time period in which a patient suffers from pain.

For the patient, it is difficult to recall the exact nature and location of pain, particularly if its occurrence happens over a long period of time. Specific periods or moments may be recalled, but details of its occurrence (e.g. time, date, place, etc), and variables (e.g. foods, medications, drugs, stress, sleep, etc) associated with it, before, during and after the occurrence of pain may go unnoticed. As this information is collected and combined with medical history records—both general and specific to the patient's condition—the patient and his/her physician or healthcare provider can make a more complete and effective diagnosis and treatment of the patient's condition.

Accordingly, there exists a need in the art for a system that allows physicians and healthcare providers to efficiently obtain pain information from patients (along with medical records) and that helps analyze and accurately display the obtained information in a manor that is meaningful to the user and/or the user's physician or healthcare provider. There also exists a need in the art for a system that allows individuals to efficiently provide such pain information and corresponding medical information.

SUMMARY OF THE INVENTION

The present invention provides a system that allows users to record information regarding the location and intensity of pain. The system also allows the user to select information that he/she, with or without the advice of his/her physician or healthcare provider, wishes to track (e.g. foods eaten, medications, drugs, moods, setting—business/leisure—, or patient/user defined items). With the user's approval, items could also be created by the user's physician or healthcare provider. Additionally, the system can present questions to the user regarding the pain experienced by the user. Questions can be of a subjective (e.g. intensity of pain) and objective (e.g. number of hours slept) nature. Some of the questions presented to the user can be selected based on previous information provided by the user. The obtained information, along with any associated information provided by the user can be graphically displayed to a physician or healthcare provider in a manner that allows the physician or healthcare provider to quickly analyze large amounts of data.

The advantages of the present invention are provided by a method of obtaining and displaying pain information. The method includes the steps receiving from a user a first set of pain information including the location and intensity of pain experienced by a user during a first time period and receiving from the user a second set of pain information including the location and intensity of pain experienced by the user during a second time period. A moving sequence of images is generated that shows changes in the pain information over time.

Pain intensity can be divided into several different levels and the images can display colors corresponding to the pain intensity levels.

The steps of receiving the first and second sets of pain information can include providing at least one diagram of the human body with an overlying grid.

BRIEF DESCRIPTION OF THE DRAWINGS

The present invention is illustrated by way of example and not limited in the accompanying figures in which like reference numerals indicate similar elements and in which:

FIG. 3 shows a web page that a patient can use to register with the pain mapping service;

FIG. 5 shows a time-sequenced series of graphical images representing pain experiences for a patient over a period of time.

DETAILED DESCRIPTION OF PREFERRED EMBODIMENTS

Figure 1:
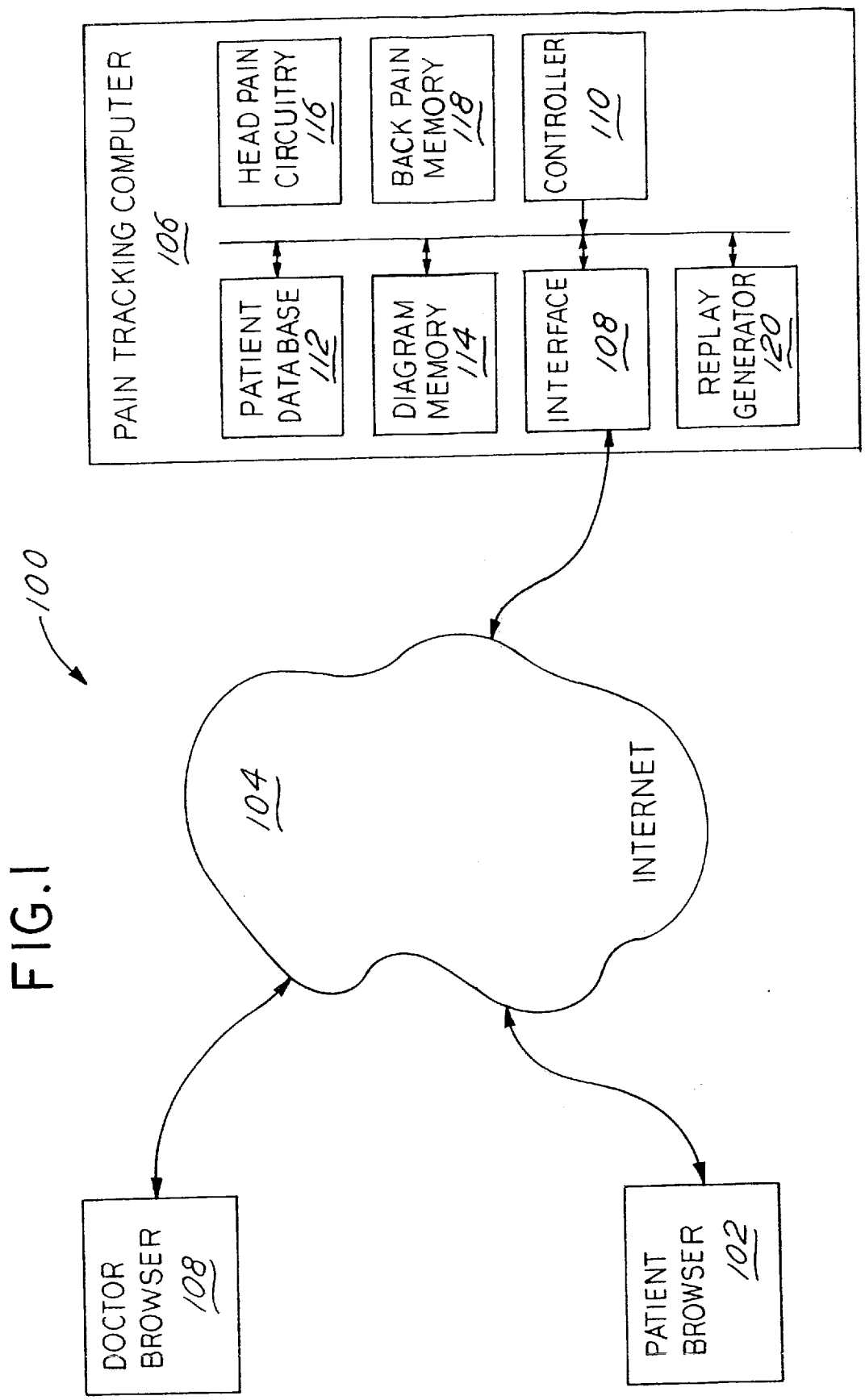
FIG. 1 shows a system for tracking and displaying pain in accordance with an embodiment of the invention.

FIG. 1 shows a system 100 for tracking and displaying pain in accordance with the present invention. A user enters information using a graphical user interface, such as through a conventional web browser 102. The entered user information travels through a computer network 104 to a pain-tracking computer 106. Computer network 104 can be any network used to connect computers together, such as the Internet. Pain tracking computer 106 contains an interface 108 for communicating with network 104 and a controller 110 for controlling the operation of the computer. The remaining modules shown in pain tracking computer 106 are described in detail below.

A physician or healthcare provider can also send and receive information to and from computer network 104 via a different web browser 108. Examples of browsers that can be used with the present invention include Microsoft Internet Explorer and Netscape Communicator. Furthermore, browsers 102 and 108 can be installed on personal computers, personal digital assistants, cellular telephones or any other wireless communication devices used to access a computer network. A replay generator 120 links together time-sequenced images of pain locations on a graphical display in order to allow a physician or healthcare provider to visually observe pain migration. The time-sequenced images can be viewed from the physician or healthcare provider's browser 108 or from another device.

Figure 2:
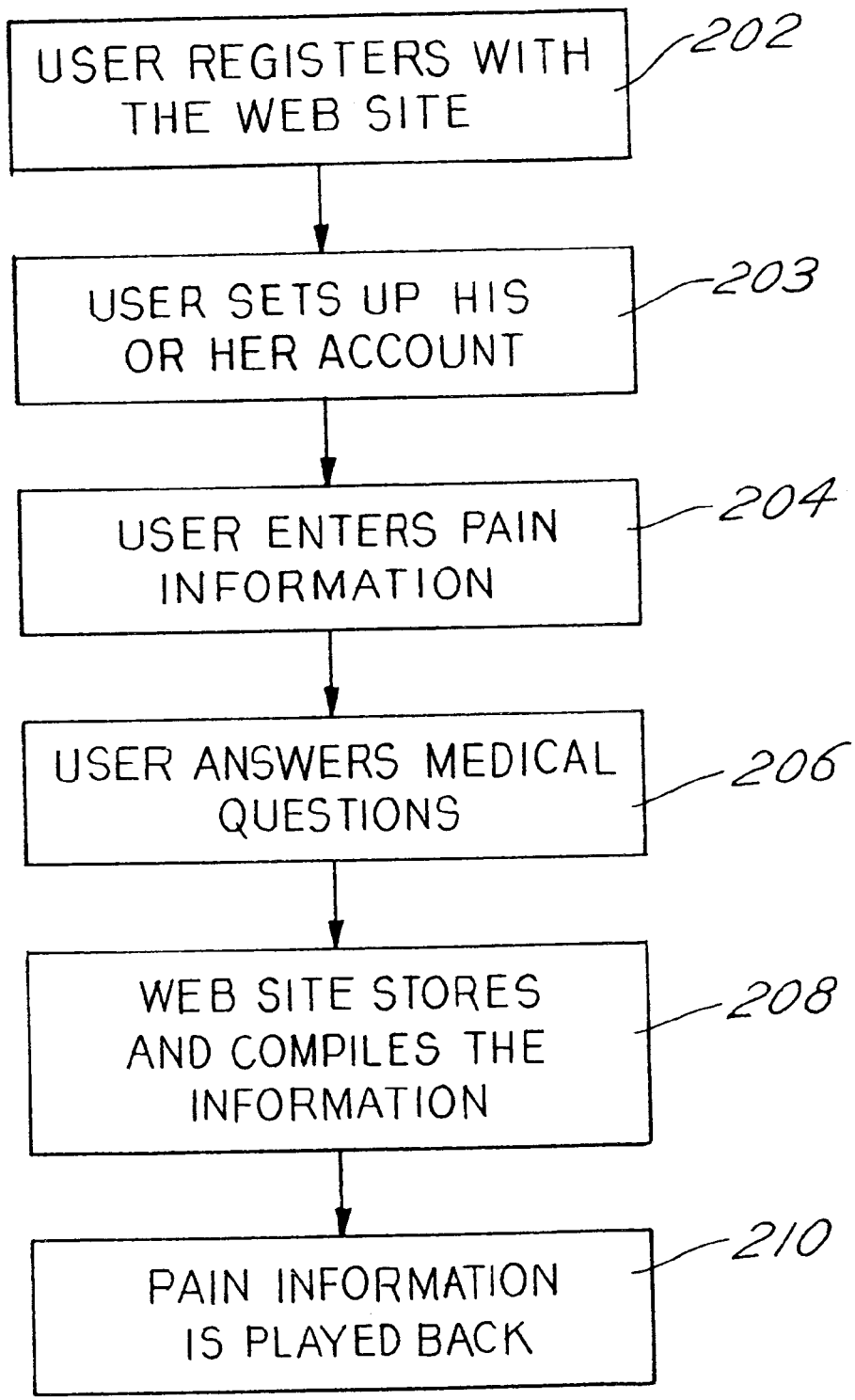
FIG. 2 shows a method for tracking and displaying pain in accordance with an embodiment of the invention.

FIG. 2 shows a method for tracking pain migration in accordance with a preferred embodiment of the invention. In step 202, the user registers with the web site. The registration step may be accomplished by telephone (e.g., by speaking to an operator or to an interactive-voice-response type system); by entering information on a web page; or any other manner that allows pain-tracking computer 106 to obtain information from the user (see FIG. 3, described in more detail below). The user may setup an account in step 203. In the setup step, the user can specify: pain tracking selection criteria (medications, foods, moods, intercourse, etc.) as well as create user definable fields if desired. The user may also set user preferences, such as links to family, friends and groups. Furthermore, the user may choose to share their information and join forums and register for other services.

In step 204, the user enters pain information graphically through a user interface that permits the user to identify the location and intensity of the pain. In step 206, the user optionally answers questions regarding the possible source and timing of the pain (e.g., associated symptoms or other information). In step 208, the pain information for the particular user is collected across a sequence of different time periods (e.g., hours, days, weeks, months or years) and stored in a secure database. Replicate copies of the database may be produced for added security, backup or re-licensing with user consent. Finally, in step 210, the collected pain information is graphically displayed in a time-sequenced format for a physician or healthcare provider to review. The playback step can be performed using a web browser, video streaming or like technology that views time-sequenced images based on the data collected by the computer.

FIG. 3 shows a web page 300 that allows a user to register with pain tracking computer 106. The user enters his or her name in block 302 and a password in block 304. The user may also provide a list of physicians or healthcare providers who may access the information provided by the user. The physicians and healthcare providers are listed in blocks 306a–306b. Box 306c may be selected to list additional physicians and healthcare providers. Furthermore, box 306d may be selected when the user wishes to not allow any physician or healthcare provider to access the information.

The user can also provide information relating to his or her condition and medical history by selecting button 308 and answering a series of questions. The questions (not shown) can elicit typical information that a user provides to a physician or healthcare provider. For example, the user may provide information relating to his or her age, weight, sex, and past medical problems and treatments. The user may also enter information relating to the medical history of family members. Finally, link 310 may be selected to set up the user's account in the manner described above.

In one embodiment of the invention, the user can identify family members or specific groups or individuals who are registered with pain tracking computer 106. Pain tracking computer 106 may then use information provided by family members or specific groups or individuals when determining which questions to ask or what information to provide. Information provided by the user can be stored in database 112. Alternatively, sensitive user information can be stored locally on the device the user uses to connect to computer network 104 to protect the user's privacy. The private information can then be retrieved when it is needed by pain tracking computer 106.

In the embodiment of FIG. 3, the user registers with pain tracking computer 106 and, as part of setting up his/her account, selects whether or not to allow his/her physician or healthcare provider to access the entered information. The user is not required to share his/her information with a physician or healthcare provider and can keep all information confidential. In one alternative embodiment, the physician or healthcare provider initially registers with pain tracking computer 106 and determines which users may utilize the services offered by pain tracking computer 106. The user can then contact pain tracking computer 106 and verify that he or she is the person that the physician or healthcare provider has authorized to utilize the services offered by pain tracking computer 106. Physician or healthcare providers might want to control access to pain tracking computer 106 to prevent people with whom they do not have a physician or healthcare provider-patient relationship from utilizing the services offered by pain tracking computer 106. Users registered with pain tracking computer 106 who have selected, either individually or through their physician or healthcare provider, to have their information shared with their physician or healthcare provider can be listed, tracked, and updated on computer 106 in order to allow the physician or healthcare provider to better follow his/her users suffering from pain.

Figure 4:
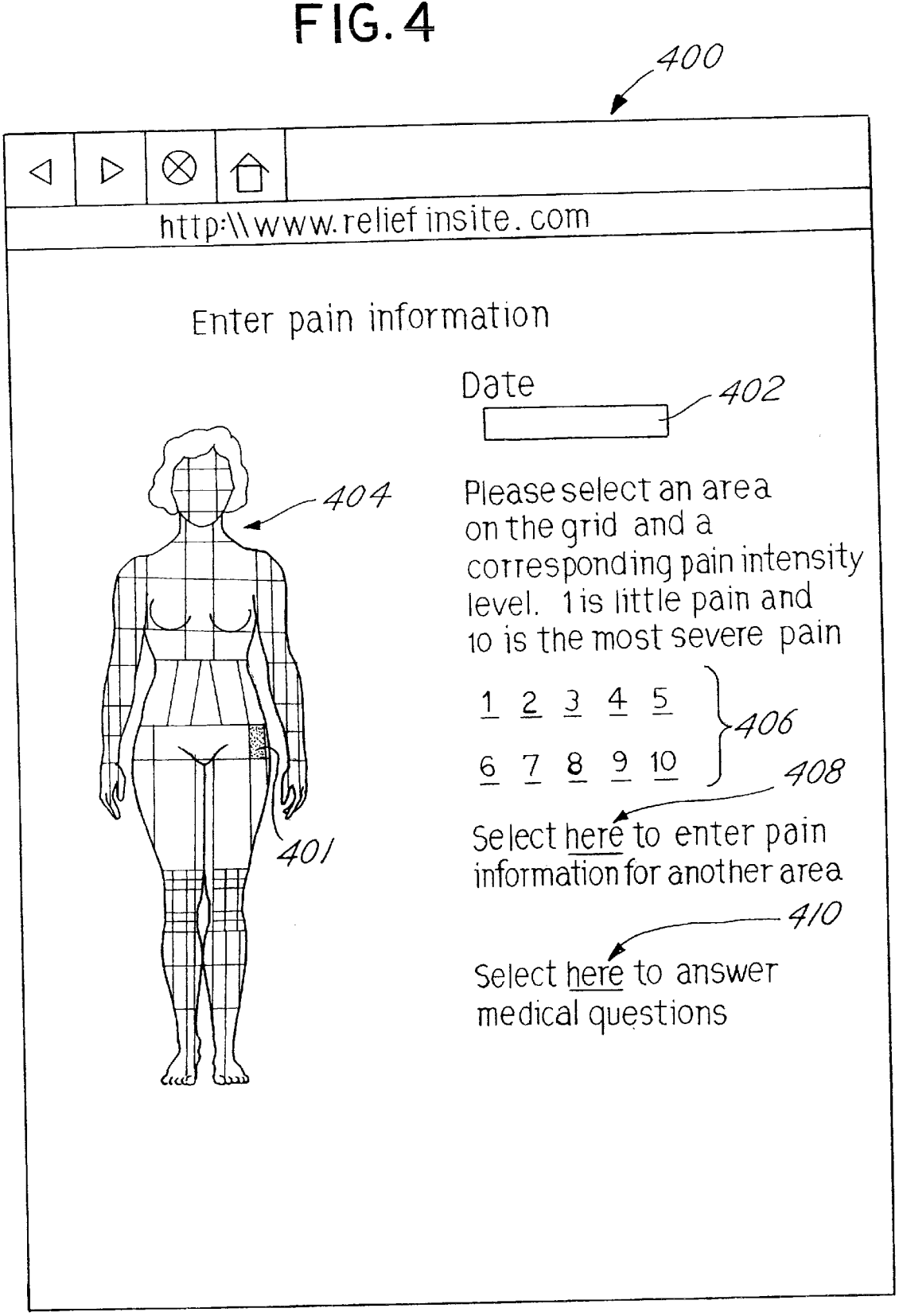
FIG. 4 shows a user interface that can be used by a patient to enter pain and related information.

FIG. 4 shows one graphical user interface in the form of a web page 400 that can be used to enter pain information. A diagram of the human body 404 is divided into a plurality of different areas by an overlying grid. In the embodiment of FIG. 4, diagram 404 divided into uneven areas, although the invention is not limited in this respect. The size and shape of the grid areas may be a function of the structure of the human body. For example, an area may correspond to the shape of a muscle that is likely to be the source of pain.

According to one aspect of the invention, the user graphically indicates one or more areas in which the user is experiencing pain (e.g., area 401). Furthermore, in one variation of the invention, after selecting one or more areas on diagram 404, diagram 404 may be replaced with another diagram (not shown) that illustrates the selected area in greater detail with another overlying grid. Greater detail may be required for portions of the body that contain small structures that are likely to be the source of pain. In another alternative embodiment, the user can position a cursor over diagram 404 and draw a shape that corresponds with the region of the user's body that is experiencing pain. The grid area(s) selected by the user are highlighted and stored in the memory of pain computer 106 for later use.

For each selected area, the user can select a corresponding pain intensity level in area 406. The corresponding area selected in diagram 404 can be color-coded with each pain intensity level having a corresponding color, so that one can look at the diagram and determine the degree of pain experienced by the user in each area. Instead of clicking on numbers, a meter or other type of graphical device can be used to enter pain intensity. In alternative embodiments, other features such as different textures or patterns may be used to distinguish between pain intensity levels.

The user, after entering the correct password and gaining access to the system, can enter the current date or a date corresponding to the information he/she is entering in text box 402. Alternatively, the computer can automatically record the current date and time as the date on which the pain occurred.

If the user is experiencing pain in more than one area, the user may select link 408 and enter additional information for other areas. Sometimes it can be difficult for users to quantify levels. Pain intensity level area 406 may also include a standardized test, such as the SF36 test. Such tests ask the user a series of questions and produce an objective value for the pain experienced by the user.

FIG. 4 shows a single diagram 404 corresponding to a female body. The sex of the diagram can be chosen based on the medical information provided by the user. Furthermore, pain-tracking computer 106 may store several different diagrams in diagram memory 114 and select a diagram based on the user's/user's sex, weight and height. Several diagrams including front, back, side and 3 dimensional views can also be used in place of diagram 404.

In FIG. 4, the user may select link 410 to answer a series of medical questions. In one embodiment of the invention, the medical questions are chosen based on the area(s) indicated on diagram 404. For example, if pain is indicated for an area frequently associated with sports injuries, the questions can be focused on likely sports activities (e.g., tennis, bicycling, or the like) that are frequently associated with a relevant type of injury that causes pain. The questions can relate to previous injuries, types of food consumed by the user or any other question that may illicit information to help diagnose the problem.

Questions can be stored in one or more memories located within pain tracking computer 106. As shown in FIG. 1, for example, questions related to head pain can be stored in a first memory area 16 and questions related to back pain can be stored in a second memory are 118. Obviously questions relating to other areas of the body can be included.

The present invention is particularly useful for diagnosing pain that migrates from one part of the body to another, such as pelvic pain. If a female user indicates that she is experiencing pelvic pain, the user may be presented with questions similar to those found on the Pelvic Pain Assessment Form distributed by the International Pelvic Pain Society. Such questions include "do you experience pain in groin when lifting" and "do you experience deep vaginal pain with sex."

The graphical user interface used to enter pain information may include several additional links. For example, web page 400 may include links to pain related forums and bulletin boards, informational resources, related services or a link to access account information.

Pain tracking computer 106 compiles the information provided by the user in step 208 and may also use known algorithms to find a correlation between the information provided by the user and the pain experienced by the user. An algorithm may determine that the day after the user sleeps less than 6 hours, the user experiences back pain 90% of the time or that the user experiences head pain every time that the user consumes Chinese food or a particular dish. Furthermore, pain-tracking computer 106 may also include information relating to typical sources of pain in different regions of the body. For example, pain-tracking computer 106 may determine that a certain pain intensity level indicated in a certain block is likely to correspond to a kidney stone. The information can be provided to the physician, healthcare provider or the user.

According to one aspect of the invention, pain information is graphically played back to the user, a physician or a healthcare provider. Turning to FIG. 5, a time-sequenced set of images shows how pain has migrated or spread from a first area 501 during a first week to a much larger area 504 by week 4. The time-sequenced images shown in FIG. 5 can be generated by a replay generator function 120 (FIG. 1) that displays dynamic changes in the pain over a period of time. The time-lapsed images can show pain intensity and location information over a period of time, and can include color-coded intensity levels indicating increasing pain intensity in addition to pain migration. The time-lapsed images can be generated and viewed using a loop-type player similar to techniques used to display time-lapsed radar images on weather maps. Alternatively, computer-generated images using an anatomically correct image of a person (e.g., with realistic skin tones and the like) can also be used.

In one embodiment of the invention, the played back sequence includes different sounds or sound levels that correspond to the indicated pain intensity. The ability to rapidly view pain migration information in an easy to understand format will aid physicians and healthcare providers in diagnosing pain problems experienced by users.

While the present invention has been described in connection with the illustrated embodiments, it will be appreciated and understood that modifications can be made without departing from the true spirit and scope of the invention.

I claim:

1. A method of obtaining and displaying pain information comprising the steps of:

(1) receiving from a user a first set of pain information including the location and intensity of pain experienced by the user during a first time period;

(2) receiving from the user a second set of pain information including the location and intensity of pain experienced by the user during a second time period; and (3) displaying a time-sequenced set of images that illustrated changes in pain location and intensity information between the first time period and the second time period.

2. The method of claim 1, wherein pain intensity is divided into several different levels and the time-sequenced set of images displays color corresponding to different pain intensity levels.

3. The method of claim 1, wherein steps (1) and (2) comprise the step of graphically entering the location of pain on a computer screen that illustrates the human body with a superimposed grid.

4. The method of claim 1, wherein the first and second sets of pain information are received at a first computer connected to a computer network and transmitted to a pain tracking computer coupled to the computer network.

5. The method of claim 4, wherein the time sequenced set of images is generated by the pain tracking computer at a location different from the first computer.

6. The method of claim 5, wherein the time sequenced set of images is displayed on a web browser and accessible by a healthcare provider at a location different from the location of the user and the location of the pain tracking computer.

7. The method of claim 1, wherein step (3) includes the step of displaying a diagram of a human body with an overlying grid.

8. The method of claim 7, wherein the time sequenced set of images comprises a diagram of the human body with colored coded sections corresponding to pain intensity levels.

9. The method of claim 1, further including the steps of:

(4) presenting a first set of medical questions to the user; and (5) receiving answers to the first set of medical questions.

10. The method of claim 9, wherein the first set of medical questions are chosen from a database of questions based at least in part on the pain information received in step (1) or step (2).

11. The method of claim 9, further including the step of presenting a second set of questions to the user, wherein the second set of medical questions are chosen from the database of questions based at least in part on the received answers to the first set of medical questions.

12. A computer programmed to perform the steps of:

(1) receiving from a user a first set of pain information including the location and intensity of pain experienced by the user during a first time period;

(2) receiving form the user a second set of pain information including the location and intensity of pain experienced by the user during a second time period; and (3) generating a time-sequenced set of images that illustrates changes in pain location and intensity information between the first time period and the second time period.

13. A method of obtaining information from a user connected to a pain tracking computer through a computer network and displaying the pain information, the method comprising the steps of:

(1) transmitting from a user computer to the pain tracking computer graphical information representing a first set of pain information including the location and intensity of pain experienced by the user during a first time period;

(2) transmitting from the user computer to the pain tracking computer graphical information representing a second set of pain information including the location and intensity of pain experienced by the user during a second time period; and (3) generating a time-sequenced set of images that illustrates changes in pain location and intensity information between the first time period and the second time period.

14. The method of claim 13, further comprising the step of viewing from a computer located at a different location from the user computer the time-sequenced set of images.

15. The method of claim 13, wherein steps (1) through (3) comprise the step of using a gender-specific diagram that has superimposed thereon a grid of predefined pain areas, wherein the gender is selected on the basis of the user's/user's gender.

* * * * *